(12) United States Patent
Harttig et al.

(10) Patent No.: US 6,287,867 B1
(45) Date of Patent: Sep. 11, 2001

(54) ASYMMETRIC POROUS MEMBRANES

(75) Inventors: Herbert Harttig, Altrip; Hartmut Merdes, Heidelberg; Hans Lange, Lampertheim; Manfred Zeiler, Altlussheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 08/296,855

(22) Filed: Aug. 26, 1994

Related U.S. Application Data (63) Continuation of application No. 08/044,128, filed on Apr. 8, 1993, now abandoned.

(30) Foreign Application Priority Data

Apr. 11, 1992 (DE) ................................................ 42 12 280

(51) Int. Cl.$^7$ .................................................... G01N 33/50
(52) U.S. Cl. .......................... 436/66; 436/169; 436/170; 422/56
(58) Field of Search ................................... 422/56, 55, 57, 422/60, 68.1, 72, 73; 436/66, 70, 518, 531, 74, 169, 170, 16

(56) References Cited

U.S. PATENT DOCUMENTS

| | | | |
|---|---|---|---|
| H623 | * 4/1989 | Miyazako | 422/56 X |
| 3,607,093 | 9/1971 | Stone et al. | |
| 4,181,500 | * 1/1980 | Cowsar et al. | 23/230 |
| 4,199,550 | * 4/1980 | Wielinger et al. | 422/58 |
| 4,294,707 | 10/1981 | Ikeda et al. | 210/782 |
| 4,307,188 | * 12/1981 | White | 435/4 |
| 4,323,536 | * 4/1982 | Columbus | 422/56 |
| 4,413,074 | * 11/1983 | Wrasidlo et al. | 524/43 |
| 4,427,416 | * 1/1984 | Bonaventura et al. | 23/293 R |
| 4,558,032 | * 12/1985 | Ecanow et al. | 514/2 |
| 4,629,563 | * 12/1986 | Wrasidlo | 210/500.34 |
| 4,774,039 | 9/1988 | Wrasidlo | 264/41 |
| 4,774,192 | * 9/1988 | Terminiello et al. | 436/530 |
| 4,806,311 | * 2/1989 | Greenquist | 422/56 |
| 4,824,639 | * 4/1989 | Hildenbrand et al. | 422/56 |
| 4,870,005 | * 9/1989 | Akiyoshi et al. | 435/7 |
| 4,898,832 | * 2/1990 | Klose et al. | 436/45 |
| 4,912,034 | * 3/1990 | Kalra et al. | 435/7 |
| 5,055,195 | * 10/1991 | Trasch et al. | 210/638 |
| 5,110,550 | * 5/1992 | Schlipfenbacher et al. | 422/56 |
| 5,114,673 | * 5/1992 | Berger et al. | 422/56 |
| 5,160,436 | 11/1992 | Hildenbrand et al. | 210/638 |
| 5,177,022 | * 1/1993 | Mangold et al. | 436/524 |
| 5,186,894 | * 2/1993 | Katsuyama | 422/56 |
| 5,187,100 | * 2/1993 | Matzinger et al. | 436/16 |
| 5,227,310 | * 7/1993 | Sakamoto et al. | 436/169 |
| 5,234,812 | * 8/1993 | Buck et al. | 435/7.5 |
| 5,234,813 | * 8/1993 | McGeeham et al. | 435/7.9 |
| 5,262,067 | 11/1993 | Wilk et al. | 210/767 |

FOREIGN PATENT DOCUMENTS

| | | |
|---|---|---|
| 0256806 | 2/1988 | (EP) . |
| 321145 | 6/1989 | (EP) . |
| 0336483 | 10/1989 | (EP) . |
| 0345781 | 12/1989 | (EP) . |
| 0407800 | * 1/1990 | (EP) . |
| 391699 | 10/1990 | (EP) . |
| 2268819 | 2/1990 | (JP) . |

\* cited by examiner

*Primary Examiner*—Jill Warden
(74) *Attorney, Agent, or Firm*—Fulbright & Jaworski, LLP (57) ABSTRACT

The invention concerns the use of an asymmetric porous membrane for the evenly distributed concentration of a substance which is not or not substantially adsorbed to the membrane and which is brought into contact with the membrane in the form of a membrane-wetting solution on the fine-pored side of the membrane.

16 Claims, 5 Drawing Sheets

ASYMMETRIC POROUS MEMBRANES

This application is a continuation of application, Ser. No. 08/044,128, filed Apr. 8, 1993 now abandoned.

The invention concerns the use of asymmetric porous membranes in analytical methods and test carriers for carrying out such methods.

The term test carrier denotes solid analytical agents, especially these which are in the form of flat strips or slides, that carry the reagents necessary for analyzes, in particular of biological liquids such as blood, plasma, serum, urine etc. The carrier materials themselves are solid and as a rule also contain the reagents in a solid form. Known carrier materials are for example fibrous structures such at paper, fleecess, woven and knitted fabrics, nets etc., films which are soluble or capable of swelling in the liquid to be examined or porous membranes The regents required for carrying out the determination of analytes in liquids such as body fluids can be manufactured by impregnating the carrier materials with appropriate solutions or coating them with appropriate spreadable pastes containing the reagents and subsequent drying. Alternatively, the required reagents can of course also be added to the carrier materials themselves during their manufacture. For example films or membranes can be manufactured from castable solutions or suspensions which already contain the reagents necessary for the determination of an analyte.

When a liquid which is to be examined is applied to such a test carrier a reaction takes place on or in the test carrier between the analyte to be determined in the sample liquid and the reagents located in the carrier material. The reaction products are determined and represent a measure of the amount of analyte in the sample liquid to be analysed.

The U.S. Pat. No. 3,607,093, for example, describes a test carrier for analysing biological liquids containing a membrane permeable to liquids which membrane contains, in at least parts, a diagnostic reagent in a solid form i.e. as a dry substance. The membrane itself should be made in such a way that at least a surface part is impermeable to larger particles such as erythrocytes. It may be gathered from the experimental section that the membrane is impregnated with a solution of the reagents necessary for analysing biological liquids and dried. When the liquid to be analysed is applied, and if desired after wiping off excess liquid, a chance in the colour of the membrane is observed if the analyte to be determined is present in the sample liquid.

EP-A 0 345 781 concerns a test carrier for analysing liquids. It contains an asymmetric porous membrane which carries one or several reagents that in the presence of the analyte to be determined produce a detectable substance. In order to determine an analyte in a liquid the sample liquid is applied to the large-pored surface of the membrane while the measurement is carried out from the fine-pored surface. The "BTS asymmetric membrane" from Filtrite (San Diego, Calif., USA) is described as being particularly advantageous since in this case cellular blood components are separated off and the reagent/analyte reaction proceeds in the entire membrane. In the selection of the reagents which generate a detectable substance on reaction with the analyte to be determined, importance is attached to the properties that are important for the detection such as colour, chemiluminescence etc, provided the reagent is sufficiently stable in the membrane.

EP-A 0 407 800 is directed towards a test strip for the analysis of substances in biological liquids. It contains an asymmetric porous membrane which is preferably manufactured from a polymer solution containing 1 to 4% by weight of an anionic surfactant. The membrane carries the reagents necessary for the analyte determination. In order to carry out the analysis, the liquid to be examined is applied to the large-pored side. The measurement of the reaction product takes place from the fine-pored side of the membrane.

None of the documents of the state of the art describe an enrichment of the detachable substance, whether it is coloured, chemiluminescent etc., on one surface of an asymmetric porous membrane containing by definition surfaces of different porosity. Surprisingly it has now been found that a substance can be concentrated and distributed evenly on the fine-pored side of an asymmetric porous membrane when this substance on the form of a membrane-wetting solution is brought into contact with the membrane and when the substance is not or not substantially adsorbed to the membrane.

The invention therefore concerns the use of an asymmetric porous membrane for the enrichment of a substance on a uniform distribution on the fine-pored side of the membrane, said substance being not or not substantially adsorbed to the membrane and brought into contact with the membrane in the form of a membrane-wetting solution.

The invention also concerns a process for the accumulation of a substance in an even distribution on one side of a membrane which is characterized in that a membrane-wetting solution of the substance is contacted with an asymmetric porous membrane on which the substance in not or not substantially adsorbed.

Finally the invention also concerns a method for the determination of a substance in a liquid sample means of a test carrier in which use is made of one of the process described above and in which a solution of the substance to be determined is contacted with an asymmetric porous membrane or the substance to be determined in the sample is formed or released by one or several of the substances present on the membrane and is determined from the fine-pored side which is characterized in that the substance to be determined is not or not substantially adsorbed to the membrane.

A particularly advantageous subject matter of the invention is a process as described above which is characterized in that the substance to be determined is haemoglobin and a suitable test carrier for this containing an asymmetric porous membrane which does not or does not substantially adsorb haemoglobin and which carries a haemolzying substance or such a substance in an additional layer located in front of it.

The term "asymmetric porous" is a conventional term generally known to a person skilled in the art (cf. for example EP-A 0 407 800 or EP-A 0 345 781). It is usually understood to be a polymer film which is porous throughout with two opposite surfaces in which the pores of one surface are larger than those of the opposite surface. Preferred asymmetric porous membranes according to the present invention are those which have an asymmetry factor of more than 10, particularly preferably of more than 100. The asymmetry factor in this case gives the ratio of the pore size on the large-pore surface to the pore size on the fine-pored surface according to the invention those asymmetric porous membranes are preferably used in which the pore size on the fine-pored side ie 0.003–3 $\mu$m.

Asymmetric porous membranes are known from the state of the art, for example from U.S. Pat. No. 4,774,039, U.S. Pat. No. 4,629,561 and also from EP-A 0 345 781. Asymmetric porous membranes can be manufactured by a person skilled in the art according to this state of the art. Asymmetric porous membranes are commercially available, for example the BTS 25 membrane of the Memtec Timonium Company, Maryland, USA has proven to be particularly advantageous according to the present invention. This membrane ie a porous polysulfone membrane. Polyethersulfone membranes alloyed with polyvinylpyrrolidone as described for example in EP-A 0 336 403 have also proven to be usable for the subject matter of the invention. Such membranes are for example cold by the X-Flow R.V. Company (Enschede, Netherlands) under the name PS 11 and PS 21.

In order to be used according to the present invention, the asymmetric porous membrane must be capable of being wetted with the liquid which contains the substance which is to be concentrated on the fine-pored side. In the case of aqueous liquids, such as body fluids like blood, plasma, serum, urine etc., the membrane must therefore be sufficiently hydrophilic. If the membrane material itself is not sufficiently hydrophilic, polymer membranes may also be hydrophiled. For this, membranes can for example be treated with those substances which are capable of swelling in water but are insoluble. It is for example known from the U.S. Pat. No. 4,413,074 that hydroxyalkyl cellulose can be used to hydrophile polymer membranes. Polyvinylpyrrolidone is also a possible hydrophiling agent.

In general a membrane ray be regarded as being sufficiently wettable by the liquid when one drop of the sample liquid having a volume of 20 $\mu$l is completely absorbed into a piece of membrane of 15 by 15 mm or larger within less than 20 sec. at room temperature and is retained in the membrane or when application of a drop of liquid to the large-pored side if an asymmetric porous membrane leads to a moistening of the membrane in the area of application through its entire thickness.

All Wettable membranes can be used according to the present invention to which the substance which is to be concentrated on the fine-pored side is not adsorbed or not substantially adsorbed. A simple test can determine whether a particular membrane-substance pair fulfills this requirement. For this the substance to be examined is dissolved in the solvent with which the concentration effect of to be achieved for example in water in the case of aqueous solutions. The solution is passed through one or several layers of the membrane under consideration and subsequently one examines whether the concentration of the substances in the solution before and after passage through the membrane is different. This can be carried out in the following manner for coloured substances five layers of an asymmetric porous membrane are clamped in a membrane filter holder (for example from the Sartorius Company, Göttingen, Germany) without a glass filter and placed on a suction bottle in such a way that the large-pored side of the membrane in each case faces upwards. The substance solution to be examined is applied to the large-pored side of the membrane in the filter holder and sucked through the membrane by applying a vacuum. After passage through the membrane, the optical density of the liquid is examined photometrically and the reading is compared with that of the original solution. Adsorption of the dissolved substance to the membrane has taken place when the optical density of the solution before and after passage through the membrane is significantly different. It is regarded as being significantly different when the optical density of the solution after passage through the membrane in at least about 15% less than the optical density of the original solution whereby the following marginal conditions have to be observed:

Concentration of the substance in the solution about 1–100 mg/l; amount of liquid to be sucked through: about 10 ml, number of membrane discs: 5 pieces; diameter of the membrane discs in the membrane filter holder: about 60 mm; thickness of the individual membrane discs: about 110 to 150 $\mu$m and speed of the suction process: about 0.25 ml/second.

Figure 1:
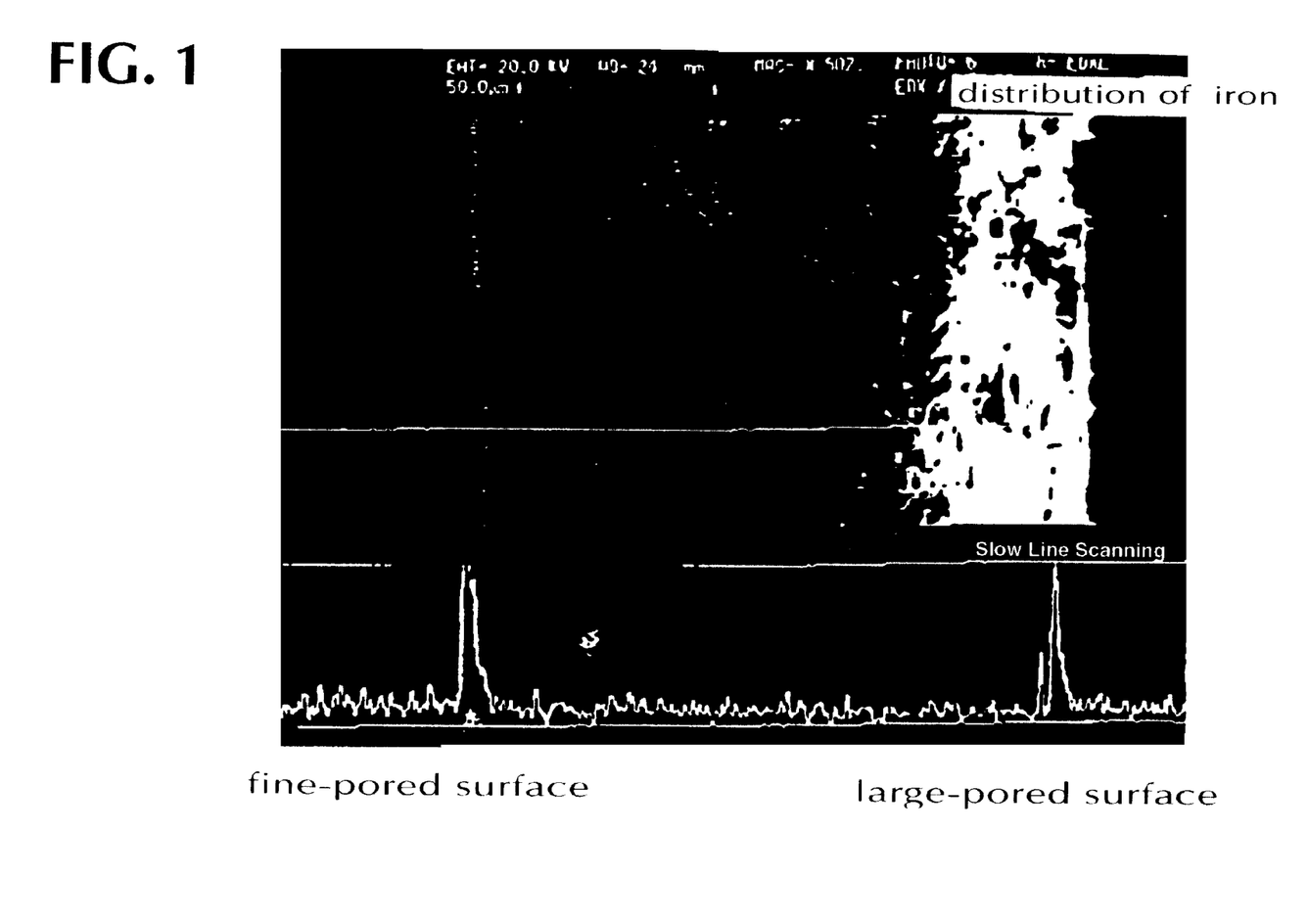
FIG. 1: Diagram of a scanning electron EDX microanalysis of a cross-section through an asymmetric porous membrane impregnated with $K_3[Fe(CN)_6]$ which is treated with carbon vapour.
Figure 2:
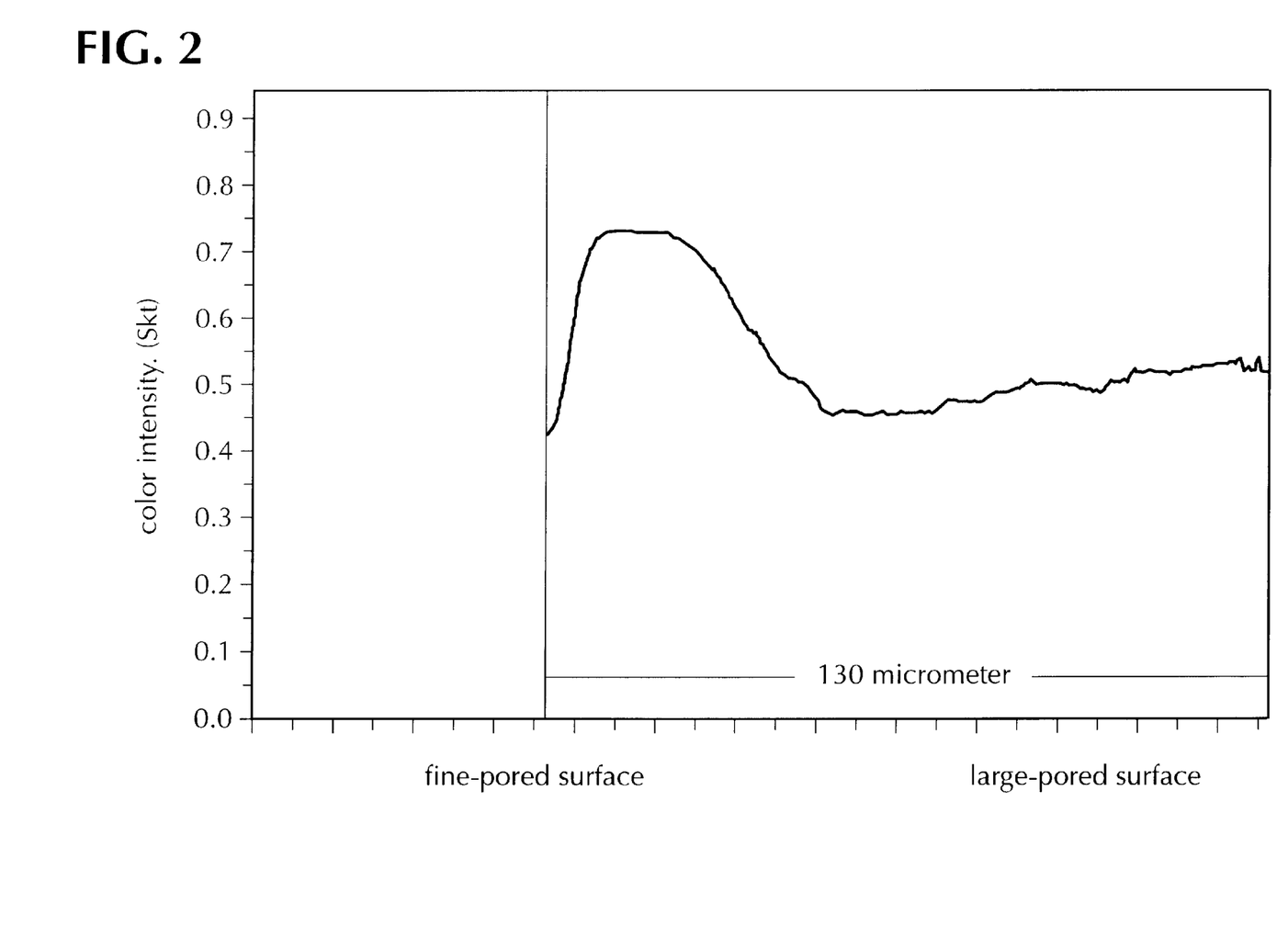
FIG. 2: Representation of the reflectance-photometric colour intensity through a cross-section of an asymmetric porous membrane impregnated with tartrazine.
Figure 3:
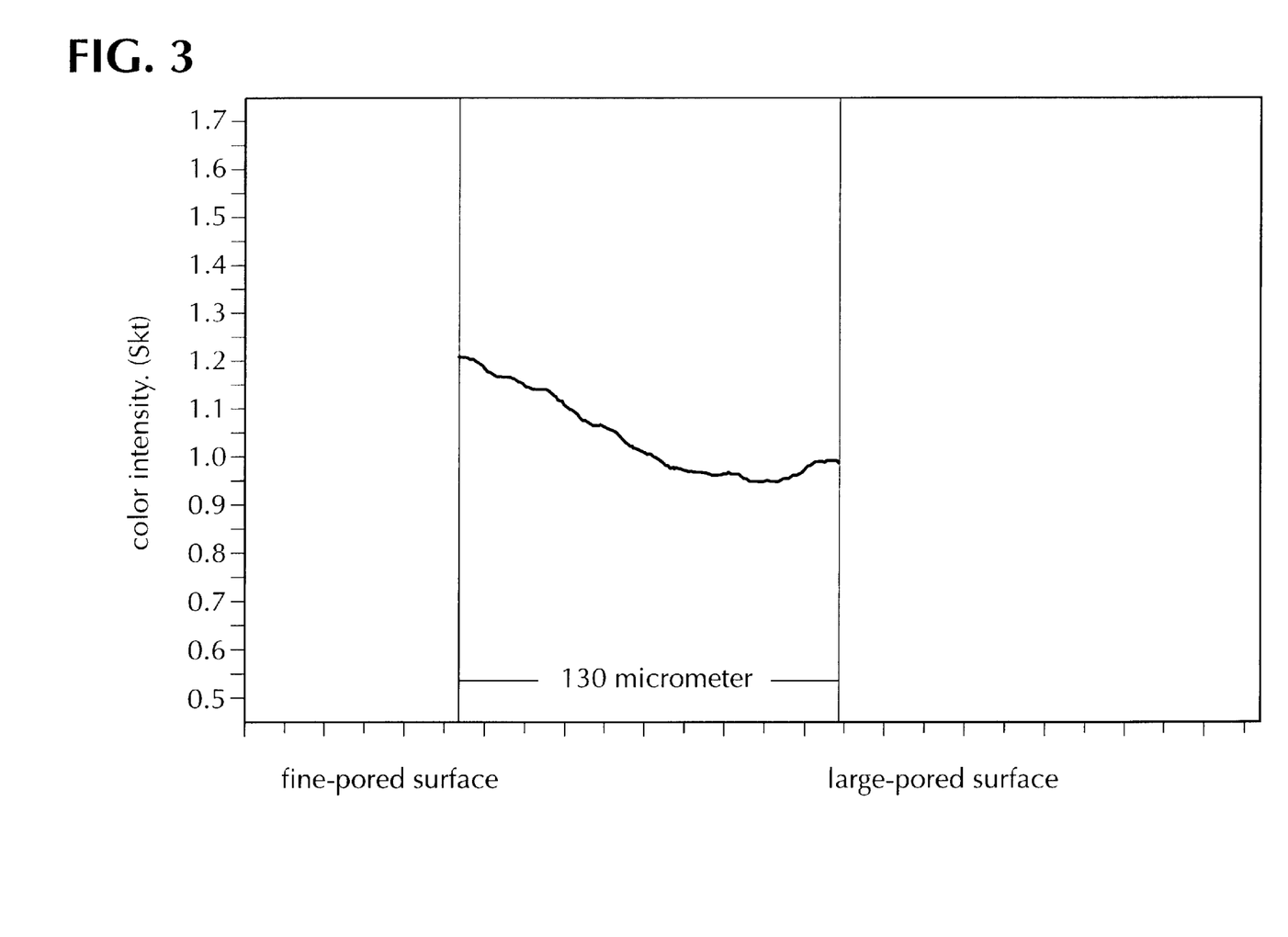
FIG. 3: Representation of the reflectance-photometric colour intensity through a cross-section of an asymmetric porous membrane impregnated with indigotin.
Figure 8:
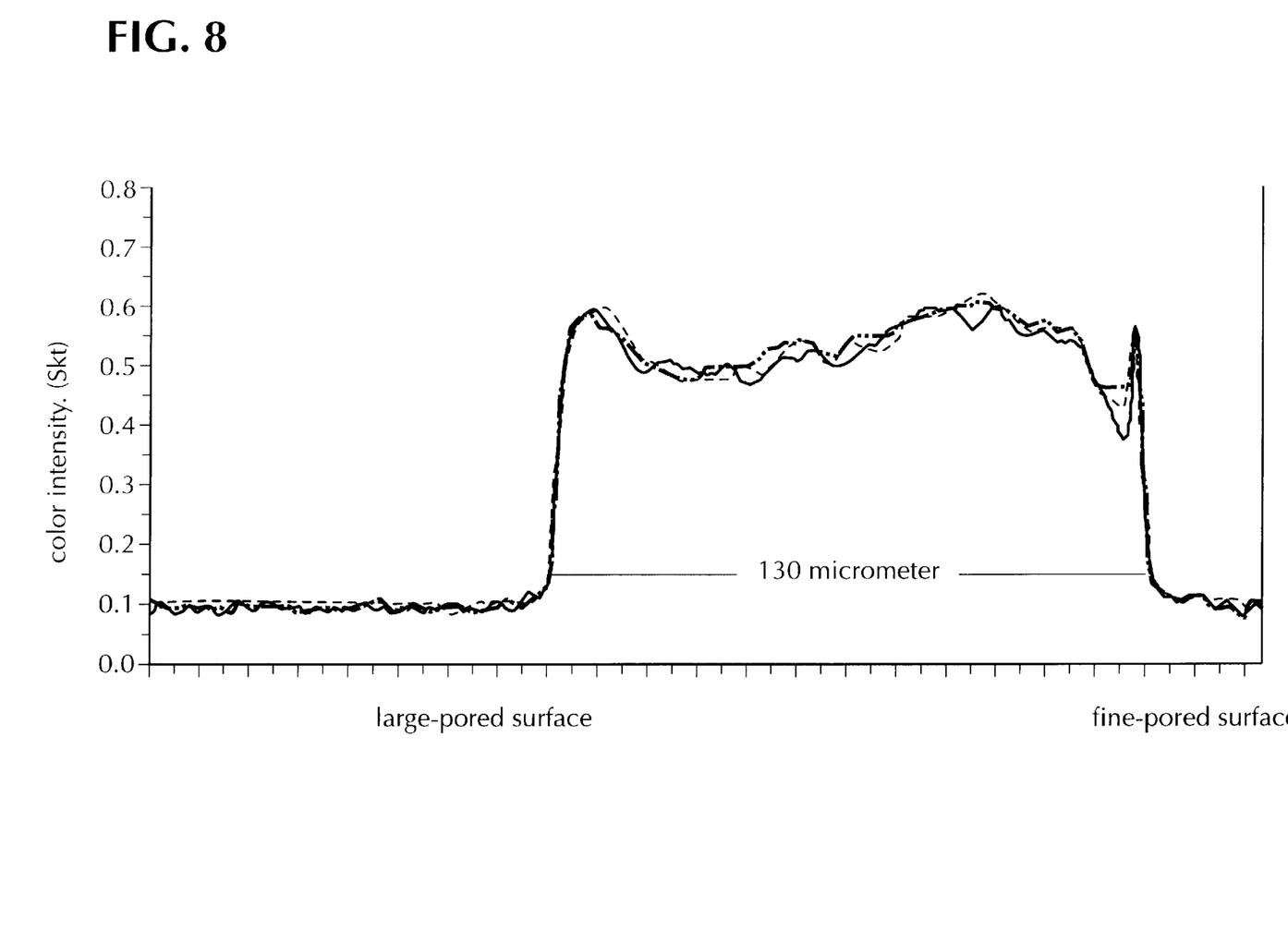
FIG. 8: Representation of the reflectance-photometric colour intensity through a cross-section of an asymmetric porous membrane impregnated with bromothymol blue.

Substances which are not or not substantially (less than 15% according to the test model described above) adsorbed to the asymmetric porous membrane are substantially concentrated on the fine-pored side of the asymmetric porous membrane, A corresponding concentration profile is shown in FIGS. 1, 2 and 3. These figures are elucidated in more detail in examples 2 and 3. A concentration profile which shows the behaviour of a substance on an asymmetric porous membrane which is adsorbed to the membrane and in not concentrated on the fine-pored side of the membrane is shown in FIG. 8. This figure is elucidated in more detail in example 10.

In order to concentrate a substance so that it is evenly distributed on the fine-pored side of an asymmetric porous membrane, a membrane-wetting solution of the substance ie brought into contact according to the present invention with the asymmetric porous membrane, This can be carried out by dipping the membrane in the solution or it is expedient to apply the solution to the membrane. When the solution is applied to the membrane it is unimportant whether the solution is applied to the fine-pored or to the large-pored side in order to achieve the concentration effect.

The process described above for concentrating a substance in a uniform distribution essentially on one side of a membrane can be used in a method for the carrier-bound determination of an analyte. For this, a solution of the substance to be determined is contacted with an asymmetric porous membrane which can be wetted by the solution and is determined on the membrane from the fine-pored side. As already set forth above it is necessary according to the present invention that the substance to be determined is not or not substantially adsorbed to the membrane. As a rule the solution of the substance to be determined is applied to the large-pored side of the membrane. However, the substance to be determined can also be released or formed by reagents located in or on the membrane or by substance which are arranged in one or several layers over the membrane. Test carrier constructions such as those known from the state of the art can in principle be used for such carrier-bound methods of determination but, however, in which according to the present invention the layer which is measured whether it be visually, optically, reflectance photometrically etc., is an asymmetric porous membrane as characterized above.

The method of determination according to the present invention is especially suitable for coloured analytes. If the substance to be determined is itself not coloured then it can be converted into coloured substances by appropriate reactions such as those which are known from analytical clinical chemistry or it can cause the formation of coloured reaction products in chemical reactions which represent a measure for the analyte to be determined.

It is advantageous for optical determinations, whether they are visual or by means of apparatus, and in particular for determinations by reflectance photometry, that the asymmetric porous membrane used according to the present invention has only of low wet transparency i.e. the reflection coefficient (percentage of reflected measurement radiation) of the membrane which is used particularly advantageously according to the present invention should be larger than 20% after wetting with the solvent of the solution to be examined and it would be even better if it were more than 50%. Also in this connection polysulfone membranes, such as for example the BTS membrane from Memtec Timonium, Maryland, USA, have proven to be advantageous for the investigation of aqueous solutions such as body fluids like blood, plasma, serum, urine etc.

The combination of the filter property of asymmetric porous membranes with low wet transparency proves to be particularly advantageous when liquid samples containing coloured particulate components have to be examined. Thus the use according to the present invention of corresponding asymmetric porous membranes is very advantageous whet applied to methods for the carrier-bound determination of substances in whole blood. When whole blood is applied to the large-pored side of an adequately hydrophilic membrane with an asymmetry factor larger than 10, preferably larger than 100, in which the pores on the fine-pored side of the asymmetric porous membrane are about 0.003 to 3 $\mu$m in size, the red blood corpuscles (erythrocytes) are prevented from reaching the fine-pored tide of the membrane. They are separated from plasma or serum which transports the dissolved sample constituents and, if desired, dissolved reagents and corresponding reaction products, by capillary force to the fine-pored side of the membrane. The substance to be determined, which was already originally present in the sample or was released or formed an the membrane by reagent contact in the sample liquid, is concentrated and spread evenly on the fine-pored side in this process if it is not or not substantially adsorbed by the membrane material.

In This manner it is possible to carry out, more sensitive determinations than would be the case without the concentration or accumulation effect. Since a uniform distribution of the substance to be determined on the fine-pored side of the asymmetric porous membrane takes place at the same time as the concentration, measurements can be carried out which have very small coefficients of variation.

The method according to the present invention for the carrier-bound determination of a substance has proven to be particularly advantageous for the determination of haemoglobin or haemoglobin derivatives from whole blood. The haematocrit, i.e. the proportion of cellular components to the volute of blood, can also be inferred from the values for the haemoglobin concentration.

Haemoglobin and haemoglobin derivatives such as for example methaemoglobin thiocyanate methaemoglobin cyanide, methaemoglobin, oxihaemoglobin or alkaline haematin are very highly concentrated on the fine-pored side when sufficiently hydrophilic asymmetric porous membranes are used.

A test carrier according to the present invention for the determination of haemoglobin or haemoglobin derivatives contains an asymmetric porous membrane as an essential component which is capable of being wetted with water, which does not substantially adsorb the haemoglobin or haemoglobin derivative to be determined and which carries a hydrolytic substance or contains such a substance in a layer arranged above the membrane. This layer may also be omitted when the haemolytic substance is added directly to the blood sample i.e. before applying the blood example to the test carrier.

Haemolytic agents are known to a person skilled in the art. For example detergents, such as anionic, cationic or non-ionogenic detergents, can be used for the test carrier according to the present invention. Examples of anionic detergents are sodium nonylsulfate, sodium dodecylsulfate, sodium dodecylsulfonate, sodium deoxycholate, sodium dioetylsulfosuccinate (DONS) or sodium diamylsulfosuccinate (DANS). Cetylapyridinium chloride, cetyldimethylethylammonium bromide or cetyltrimethylammonium bromide can for example be used as cationic detergents. Examples of non-ionogenic detergents include polyoxyethylene ethers. A substance or a mixture of several substances can be used according to the present invention an the haemolytic agent.

The test carrier according to the present invention can carry the haemolytic agent directly on the asymmetric porous membrane or it can be located in a further layer which is arranged above the large-pored side of the asymmetric porous membrane. If it is not intended to use a further layer for the haemolytic agent, it is then expedient to apply the haemolytic agent to the asymmetric porous membrane by impregnation. It is also possible to apply the haemolytic agent to the large-pored side of the membrane in a spreadable pact; and to dry it there. If a separate layer is used, a suitable carrier material can likewise be impregnated with a solution of the haemolytic agent or coated with a spreadable paste of the haemolytic agent. In this case the type of carrier material is not important, provided it does not interfere with the determination reaction. Conceivable interferences are for example adsorption of haemoglobin to the carrier material or interfering reactions of the carrier material with haemoglobin or haemoglobin derivatives. A glass fibre fleece has, for example, proven to be suitable.

Buffer substances and substances which lead to an oxidation or complexing of haemoglobin have proven to be advantageous additives to the haemolytic agent. Buffer substances which come into consideration in this connection are those which can set a pH value in the range of 2–12, preferably 6–8. In this regard phosphate buffer (pH 5–8), citrate buffer (pH 2–8) and citrate-phosphate-borate buffer (pH 2–13) are particularly advantageous.

All substances which oxidize iron but do not destroy the haemoglobin structure can be used to oxidize haemoglobin. Higher-valent metal salts and metal complex compounds have proven to be particularly advantageous whereby potassium hexacyanoterrate (III) is especially preferred. Substances selected from the group comprising halogenides and pseudohalogenides can be used to complex the haemoglobin formed in this process. The use of cyanides, fluorides or thiocyanates has proven to be particularly advantageous, However, the method according to the present invention in also suitable for detecting non-complexed hemoglobin.

In an advantageous embodiment or a test carrier according to the present invention for the determination of haemoglobin, the asymmetric porous membrane is arranged on a stiff material such as a plastic foil so that the test carrier can be handled more easily and simply and in order that the asymmetric porous membrane does not have to be touched with the fingers when carrying out the test. In this case the asymmetric porous membrane is attached to this support in such a way that either the application of the sample to be examined or the determination can take place on the surface of the asymmetric porous membrane which faces the carrier. When the sample is applied to the surface of the asymmetric porous membrane facing the support this means that the stiff supporting material has to be permeable to the sample. In the simplest case there is a hole in the support and under the hole the asymmetric porous membrane is attached in such a way that the sample can be applied to the membrane through the hole.

If the surface of the asymmetric porous membrane from which the measurement ie to take place faces the support, the support should not interfere with this measurement. For this it is possible that the support be transparent to light for optical Measurement methods. Also, in this case, a further possibility is that a hole is located in the support and that the membrane be attached to the support material over this hole in such a way that the appropriate surface of the asymmetric porous membrane can be measured.

Figure 4:
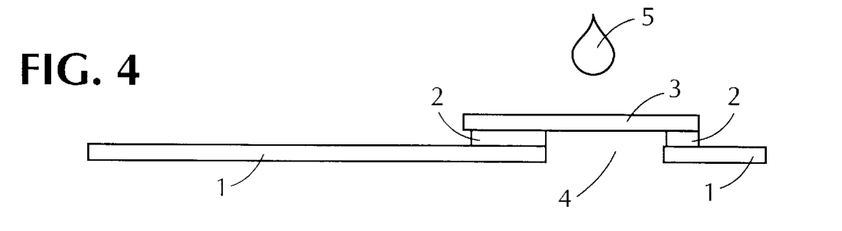
FIGS. 4–6: Cross-sections through advantageous embodiments of test carriers according to the present invention.
Figure 5:
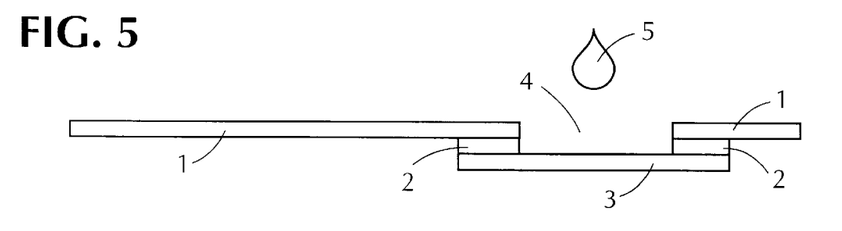
Figure 6:
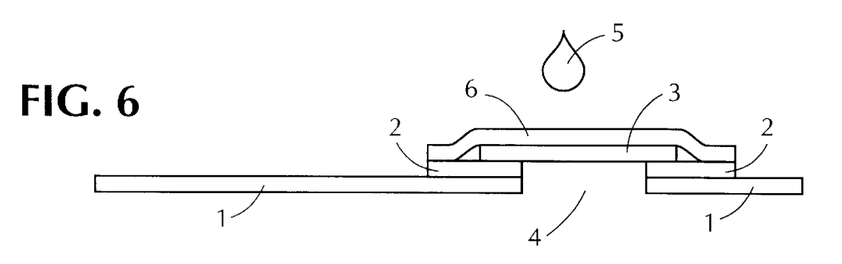
Figure 7:
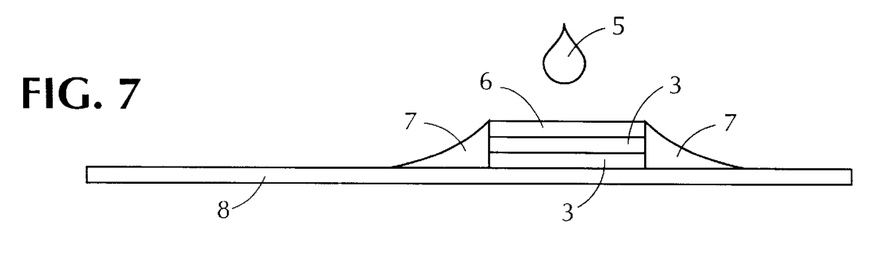
FIG. 7: Cross-section through a test carrier which demonstrates the even distribution of a substance on the fine-pored side of an asymmetric porous membrane.

Advantageous embodiments of test carriers according to the present invention for the determination of haemoglobin are shown in FIGS. 4, 5 and 6. FIG. 7 shows a toot carrier which can be used to demonstrate the uniform distribution of a substance on the fine-pored side of an asymmetric porous membrane.

The test carrier according to FIG. 4 is composed of a strip (1) made or a stiff material such as for example a plastic foil with a hole (4). An asymmetric porous membrane (3) which is attached to the strip (1) with a double-sided adhesive tape (2) is located above the hole (4). The asymmetric porous membrane (3) in mounted in such a way that its fine-pored side is facing the strip (1). Similar test carrier constructions are for example known from EP-A 0 256 806 or EP-A 0 407 800. However, in contrast to the State of the art the test carrier for the determination of hemoglobin according to the present invention contains a haemolytic agent as well as, if desired, further substances such as for example buffer substances and/or agents which oxidize or complex haemoglobin in the asymmetric porous membrane (3). Blood (5) is applied to the large-pored side of the asymmetric porous membrane (3), the erythrocytes are haemolyzed in the membrane (3) and the released haemoglobin or corresponding haemoglobin derivatives, when for example oxidizing or complexing substances are present as additional reagents, is concentrated and spread evenly in the membrane (3) on the fine-pored side of the asymmetric porous membrane (3). The concentration of haemoglobin or of the haemoglobin derivatives is determined through the hole (4) on the fine-pored side of the asymmetric porous membrane (3).

The test carrier according to FIG. 5 differs from that of FIG. 4 in that the asymmetric porous membrane (3) is attached to the strip (1) in such a way that the large-pored surface of the membrane (3) faces the strip (1). Blood (5) is applied through the hole (4) onto the large-pored side of the asymmetric porous membrane (3). The measurement is carried out from the fine-pored surface of the membrane (3) which is the side opposite to the hole (4).

A test carrier is shown in FIG. 6 which has a layer (6) over the large-pored surface of the asymmetric porous membrane (3) which can be impregnated with all or with some of the reagents necessary for the test. This layer (6) can for example contain substances necessary for the haemolysis of erythrocytes. When blood (5) is applied to the layer (6) these substances are dissolved and together with the sample liquid reach the membrane (3). The test reaction is observed from the fine-pored side of the membrane (3) through the hole (4).

A test carrier is shown in FIG. 7 in which an asymmetric porous membrane (3) is attached to a strip (8) made of a stiff, translucent material by means of hot-melting adhesive (7) which is mounted in such a way that the fine-pored surface faces the strip (8). A layer (6), for example a glass fibre fleece, is mounted above the membrane (3) in such a way that it does not touch the membrane (3) but can be brought into contact with it by pressure from above. Thus in the initial position there is a gap (9) between the membrane (3) and layer (6). After application of the liquid sample to the layer (6) the sample remains there without entering into the membrane (3). The residence time can be selected as desired. Only when pressure is applied to the layer (6) so that this layer is brought into contact with the membrane (3) can the liquid from the layer (6) enter into the membrane (3). The fine-pored side of the asymmetric porous membrane (3) can be observed through the translucent strip (8). The concentration of a detectable substance can be measured through the strip (8) in this manner.

The invention is elucidated in more detail by the following examples which, however, are not intended to be understood as a limitation of the invention to these concrete embodiments.

EXAMPLE 1 a) 10 µl of different dye solutions are applied to the large-pored side of an asymmetric porous membrane (BTS 25, manufactured by Memtec Timonium Company, Maryland, USA).

Preparation of the Dye Solutions:
1. Indigotin (manufacturer Aldrich, Steinheim, Germany, catalogue No. 22,929-6)
   Stock solution: dissolve 20 mg/10 ml water
   Dilution: dissolve 10 µl stock solution in 20 ml water
   Concentration of the dye solution=1 mg/l
2. Toluidine blue (manufacturer Fluka, Buchs, Switzerland, catalogue No. 89640)
   a) In ethanol:
   Stock solution: dissolve 20 mg/10 ml ethanol
   Dilution: dissolve 100 µl stock solution in 10 ml ethanol
   Concentration of the dye solution=20 mg/l
   b) In water:
   Stock solution: dissolve 20 mg/10 ml water
   Dilution: dissolve 100 µl stock solution in 10 ml ethanol
   Concentration of the dye solution=20 mg/l
3. Rhodamine B (manufacturer Aldrich, Steinheim, Germany, catalogue No. 25,242-5)
   Stock solution: dissolve 12.5 mg in 10 ml ethanol
   Dilution: dissolve 100 µl stock solution in 10 ml ethanol
   Concentration of the dye solution=1.25 mg/l
4. Coomassie blue (manufacturer Serva, Heidelberg, Germany, catalogue No. CJ42655)
   Stock solution: dissolve 20 mg in 8 ml ethanol.
   Dilution: dissolve 70 µl stock solution in 10 ml ethanol.
   Concentration of the dye solution=17.5 mg/l
5. Tartrazine (manufacturer Serva, Heidelberg, Germany, catalogue No. CJ19140)
   Stock solution: dissolve 20 mg in 2 ml water
   Dilution: dissolve 50 µl stock solution in 10 ml water
   Concentration of the dye solution=50 mg/l
6. Safranin (manufacturer Aldrich, Steinheim, Germany, catalogue No. 10,214-8)

a) In ethanol:
   Stock solution: dissolve 20 mg in 10 ml ethanol
   Dilution: dissolve 100 μl stock solution in 10 ml ethanol
   Concentration of the dye solution=20 mg/l
b) In water:
   Stock solution: dissolve 20 mg in 10 ml water
   Dilution: dissolve 100 μl stock solution in 10 ml water
   Concentration of the dye solution=20 mg/l
7. Acid green 41 (manufacturer Aldrich, Steinheim, Germany, catalogue No. 21,071-4)
   Stock solution: dissolve 20 mg in 10 mg ethanol
   Dilution: dissolve 400 μl stock solution in 10 ml ethanol
   Concentration of the dye solution=80 mg/l
8. Bromothymol blue (manufacturer E. Merck, Darmstadt, Germany, catalogue No. 3026)
   Stock solution: dissolve 10 mg in 5 ml buffer, pH 9
   Dilution: dissolve 40 μl stock solution in 10 ml buffer
   Concentration of the dye solution=8 mg/l
9. Potassium hexacyanoferrate III (manufacturer Aldrich, Steinheim, Germany, catalogue No. 22,768-4)
   Stock solution: dissolve 20 mg in 10 ml 0.1 N phosphate buffer, pH 3
   Concentration of the dye solution=2000 mg/l
   On the basis of the colour impression which forms on the fine-pored side after application of the solution to the large-pored side it is possible to judge whether a concentration has taken place on the fine-pored side (see table of results).
b) Filtration experiments are carried out to examine the adsorption or non-adsorption of substances to membranes. For this the colour solutions from a) are filtered through several layers of membranes. The concentrations of dye in the solutions before and after filtration is determined photometrically.

Procedure for the Measurements 2 ml are withdrawn from 10 ml of the respective dye solution and measured in a 10 mm cuvette using a UV/VIS spectrometer, model 845 A, Hewlett Packard Company in comparison with a pure solvent.

Discs are punched from a BTS25 membrane (Memtec Timonium Company, MD, USA) with a diameter of 60 mm. For each adsorption experiment a pile of 5 membrane discs with the large-pored side facing upwards was clamped in a membrane filter holder of the Sartorius Company (Göttingen, GFR). The glass frit was removed beforehand from the filter holder.

The filter holder was placed on a suction bottle. The remaining 8 ml dye solution was sucked through the membrane layers by applying a low vacuum. The filtrate was then measured in a corresponding manner to that of the initial solution. The concentrations were calculated from the absorbances.

Results:

| Dye | Solvent | Concentration | Absorbance Before filtration in % | Absorbance After filtration in % | Concentration Before filtration in mg/l | Concentration After filtration in mg/l | % Difference |
|---|---|---|---|---|---|---|---|
| Indigotin | water | + | 0.055 | 0.050 | 1 | 0.9 | −8.78 |
| Toluidine blue | ethanol | + | 1.124 | 1.08 | 20 | 19.22 | −3.9 |
|  | water | − | 0.47 | 0.392 | 20 | 16.68 | −16.6 |
| Rhodamine B | ethanol | + | 0.329 | 0.327 | 1.25 | 1.2 | −0.8 |
| Coomassie blue | ethanol | + | 0.68 | 0.682 | 17.5 | 17.55 | +0.2 |
| Tartrazine | water | + | 0.242 | 0.241 | 50 | 49.79 | −0.4 |
| Safranine | ethanol | + | 0.79 | 0.79 | 20 | 20 | 0.0 |
|  | water | − | 1.59 | 1.33 | 20 | 16.73 | −16.35 |
| Acid green | ethanol | + | 0.824 | 0.821 | 80 | 79.71 | −0.36 |
| Bromothymol blue | buffer pH 9 | − | 0.289 | 0.163 | 8 | 4.51 | −43.6 |
| Potassium hexacyano-ferrate (III) | 0.1 N phosphate buffer pH 3 | + | 0.383 | 0.382 | 2000 | 1995.3 | −0.23 |

It turned out that all dyes whose concentration decreased by less than 15% produced the discovered concentration effect while those dyes whose concentration decreased more did not exhibit the effect.

c) The investigation whether the tested solutions wetted the membrane is carried out as follows: A drop of the solution of 20 μl volume is placed on the large-pored side of a 15×15 mm membrane. The time required for a complete absorption is measured. The experiment is repeated with the difference that it is applied to the fine-pored side. If both times are under 20 sec the solutions are considered as being wetting.

EXAMPLE 2

An asymmetric porous membrane BTS 25 (Memtec Timonium Company, MD, USA) was impregnated with a solution of 1% sodium dodecylsulfate, 0.1 N phosphate buffer, pH 7 and 0.7 mmol/l $K_3Fe(CN)_6$. The uptake of liquid was calculated as 115 ml/m². The membrane loaded with liquid was dried for 30 minutes at 50° C. After cooling with liquid nitrogen the impregnated membrane was broken. The cross-section was treated with carbon vapour and examined for iron in a scanning electron microscope with EDX microanalysis of the Cambridge Co., Nußloch, Germany.

It can be demonstrated that iron was strongly concentrated on the fine-pored side of the membrane (FIG. 1). This was confirmed visually by significant differences in the yellow colour of the fine-pored and the large-pored side. Iron signals on the large-pored side resulted by viewing the surface when slightly tilting the sample in the measurement holder.

EXAMPLE 3

In order to examine dyes concentrated on the fine-pored side of an asymmetric porous membrane, cross-sections of BTS 25 membranes (Memtec Timonium Co. MD, USA) were prepared after contacting them with the respective dye solutions from example 1. For this the membranes were cut with a new razor-blade. The cross-section was photographed in a light microscope with an attached colour video printer and printed as an enlarged video print. The colour print was subsequently scanned on a reflectance-photometric scanner, Elscript 400, Hirschmann Co., Germany. A mean was taken from 4 measurement tracs. By this means it was possible to quantitate the optical impression. The results of tartrazine are shown in FIG. 2 and those of indigotin are shown in FIG. 3 as examples of substances which are concentrated. The coarse structure on the large-pored side gives the illusion of more colour in the diagram than is in fact present since black is also interpreted as colour by the scanner.

EXAMPLE 4

10 µl methaemoglobin cyanide solution (7 g/dl) is applied to the large-pored side of a 12×8 mm asymmetric membrane (BTS 25, Memtec Timonium, Maryland, USA). The reflectance on the fine-pored side was measured after 8 seconds at 567 nm. With 50 measurements a mean reflectance of 40.25% with a coefficient of variation of 1.14% was observed.

EXAMPLE 5

An asymmetric porous membrane (BTS 25, Memtec America Corp. Timonium, Maryland, USA) with a width of 28 cm was impregnated in a solution of 1% by weight sodium dodecylsulfate, 0.1 N phosphate buffer, pH 7 and 0.7 mmol/l potassium hexacyanoferrate (III). The uptake of liquid was about 115 ml/m$^2$. The membrane loaded with liquid was dried for 30 minutes at 50° C. The dry membrane was cut into 8 mm wide strips, and glued onto a 420 µm thick PVC foil provided with a 6 mm diameter hole in the region of the membrane application by means of a double-sided adhesive tape in such a way that the membrane was not covered by the double-sided adhesive tape in the region of the hole. The orientation of the asymmetric membrane was chosen so that the fine-pored side faced the hole (cf. FIG. 4). Subsequently ca. 10 µl whole blood was applied to the large-pored side of the membrane in the region of the hole. The spotted test strip was inserted into a suitable measuring instrument and measured on its fine-pored side after 44 seconds. Between sample application and measurement time a uniform dark colouration forms on the fine-pored side. Although the test device does not include any additional measures whatsoever for the distribution of the blood on the application side, an unexpectedly high precision of the results was achieved. The coefficient of variation was 1.6% with n=10 (n=number of measurements).

EXAMPLE 6

A test strip structure analogous to example 5 was constructed with the difference that the large-pored side of the membrane faced the hole (cf. FIG. 5). The blood was applied through the hole in the carrier foil. This simplified somewhat the accuracy when applying the sample. The measurement was carried out from the fine-pored side. The results were comparable with those from example 5.

EXAMPLE 7

A test strip structure analogous to example 5 (corresponding to FIG. 4) was constructed with the difference that the impregnation solution had the following composition:

0.3% by weight sodium dioctylsulfosuccinate (DONS) (E. Merck, Darmstadt, Germany), 0.3% by weight sodium diamylsulfosuccinate (DANS) (Cyanamid, Wolfratshausen, Upper Bavaria, Germany), 0.2% by weight saponin 0.2% by weight potassium hexacyanoferrate (III) in 0.1 mol/l citrate buffer, pH 6.8

The measurement was carried out analogous to example 5. In this case the coefficient of variation was 1.25% with n=10.

EXAMPLE 8

An asymmetric porous membrane (BTS 25) was mounted in a test strip between a clear transparent 200 µm thick foil (Pokalon, Lonza, Weil am Rhein, Germany) and a glass fibre fleece (Trapo 83/14, J.C. Binzer Co., Hatzfeld/Eder, Germany) in such a way that the large-pored side faced the glass fibre fleece but so that there was no contact between the membrane and the glass fibre fleece (cf. FIG. 7). The glass fibre fleece was impregnated with methaemoglobin cyanide. After completion of the impregnation, the test strip was measured by reflectance photometry at 567 nm in a suitable instrument. In doing so mechanical contact was made between the impregnated glass fibre fleece and the asymmetric membrane before beginning the measurement by the measuring device. A reflectance of 32.69% was observed at a methaemoglobin cyanide concentration of 7 g/dl. The coefficient of variation was 1.77%.

EXAMPLE 9

The experiment of example 8 was repeated but without the membrane between the glass fibre fleece and the transparent foil. With this procedure the results showed a coefficient of variation of 5.84%.

A comparison of examples 8 and 9 clearly shows that the membrane used leads to a better uniformity of the colour reproduction. The application is not limited to analytical methods for determining haemoglobin in blood but can be applied in all cases where it is necessary or desirable to increase the homogeneity of a colour impression.

EXAMPLE 10

Bromothymol blue was examined analogously to example 3 as a substance which does not concentrate on the fine-pored side of an asymmetric porous membrane. After contact with corresponding dye solution, the impregnated and dried BTS 25 membrane (Memtec Timonium Co., MD, USA) was immersed in liquid paraffin (melting point 56–58° C., E. Merck, Darmstadt, Germany) and subsequently allowed to drain. By this means the membrane was coated with a thin paraffin layer which stabilizes the structure but which does not dissolve the dye or the membrane itself.

A concentration profile was constructed analogously to example 3. FIG. 8 shows that the colour intensity and thus the dye concentration is substantially constant throughout the thickness of the membrane.

What is claimed is:

1. In a method of detecting haemoglobin or a haemoglobin derivative comprising contacting a liquid sample containing haemoglobin or a haemoglobin derivative with a test carrier and detecting said haemoglobin or said haemoglobin derivative, the improvement comprising:

contacting said liquid sample containing said haemoglobin or said haemoglobin derivative with an asymmetric porous membrane having a fine pored side and a large pored side, wherein said haemoglobin or said haemoglobin derivative concentrates in the fined pored side of said asymmetric porous membrane and said asymmetric porous membrane does not adsorb or does not substantially adsorb said haemoglobin or said haemoglobin derivative.

2. The method of claim 1, wherein said asymmetric porous membrane has an asymmetric factor of greater than 10.

3. The method of claim 1, wherein said asymmetric porous membrane has a pore size on the fine-pored side or about 0.003 to 3 microns.

4. The method of claim 1, wherein said asymmetric porous membrane has a reflection coefficient of greater than 20%, after contacting said aqueous porous membrane with a liquid solution in the absence of hemoglobin or a hemoglobin derivative.

5. The method of claim 1 wherein an oxidizing or complexing substance is present on the membrane and the wetting sample contains a haemoglobin derivative.

6. A method for determining the presence of haemoglobin or a haemoglobin derivative in a liquid sample, comprising:
   a) contacting a liquid sample containing said haemoglobin or said haemoglobin derivative with an asymmetric porous membrane, wherein said asymmetric porous membrane has a fine pored side and a large pored side and does not adsorb or does not substantially adsorb said haemoglobin or said haemoglobin derivative; and
   b) detecting the presence of said haemoglobin or said haemoglobin derivative optically, visually, or reflectance photometrically from said fine-pored side.

7. The method of claim 6, wherein said asymmetric porous membrane has an asymmetric factor greater than 10.

8. The method of claim 6, wherein said asymmetric porous membrane has a pore size on the fine-pored side of about 0.003 to 3 microns.

9. The method of claim 6, wherein said asymmetric porous membrane has a reflection coefficient of greater than 20%, after contacting said aqueous porous membrane with a liquid sample in the absence of an haemoglobin or a haemoglobin derivative.

10. The method of claim 5, wherein said hemoglobin is released from erythrocytes or a hemoglobin derivative is formed from hemoglobin after the liquid sample containing the erythrocytes or hemoglobin contacts the asymmetrical porous membrane.

11. The method of claim 5, wherein said hemoglobin is released from erythrocytes or a hemoglobin derivative is formed from hemoglobin after the liquid sample contacts, at a time prior to the contact of liquid to the asymmetric porous membrane, a layer which is different from the asymmetric porous membrane.

12. The method of claim 6 wherein an oxidizing or complexing substance is present on the membrane and the liquid sample contains a haemoglobin derivative.

13. A method for determining the presence of haemoglobin or a haemoglobin derivative in a liquid sample, comprising:
   a) reacting a liquid sample containing said haemoglobin or said haemoglobin derivative with a hemolytic agent to release haemoglobin or said haemoglobin derivative;
   b) contacting said liquid sample containing said haemoglobin or said haemoglobin derivative to an asymmetric porous membrane which has a fine-pored side and a large pored side and does not adsorb or does not substantially adsorb said haemoglobin or said haemoglobin derivative; and
   c) detecting the presence of said haemoglobin or said haemoglobin derivative optically, visually, or reflectance photometrically, from said fine pored side.

14. The method of claim 13 wherein an oxidizing or complexing substance is present on the membrane and the liquid sample contains a haemoglobin derivative.

15. A method for determining the presence of haemoglobin or a haemoglobin derivative in a liquid sample, comprising:
   a) contacting a liquid sample containing said haemoglobin or said haemoglobin derivative with an asymmetric porous membrane which has a fine-pored side and a large pored side, carries a hemolytic reagent which forms a detectable analyte with said haemoglobin or said haemoglobin derivative, and does not adsorb or does not substantially adsorb said haemoglobin or said haemoglobin derivative; and
   b) detecting the presence of said haemoglobin or said haemoglobin derivative optically, visually, or photometrically, from said fine pored side.

16. The method of claim 15 wherein an oxidizing or complexing substance is present on the membrane and the liquid sample contains a haemoglobin derivative.

* * * * *